US011696845B2

(12) United States Patent
Burton et al.

(10) Patent No.: US 11,696,845 B2
(45) Date of Patent: Jul. 11, 2023

(54) SHOULDER BRACE DEVICE

(71) Applicant: Burton Braces, LLC, Oxford, MS (US)

(72) Inventors: Scott Burton, Oxford, MS (US); John Atallah, San Mateo, CA (US); Edwar Abboud Habr, San Mateo, CA (US); John Robert Burnett, Oxford, MS (US); Tal Hendrix, Jackson, MS (US)

(73) Assignee: Burton Braces, LLC, Oxford, MS (US)

( * ) Notice: Subject to any disclaimer, the term of this patent is extended or adjusted under 35 U.S.C. 154(b) by 0 days.

(21) Appl. No.: 17/241,659

(22) Filed: Apr. 27, 2021

(65) Prior Publication Data

US 2022/0339019 A1    Oct. 27, 2022

(51) Int. Cl.
*A61F 5/02* (2006.01)
*A61F 5/01* (2006.01)

(52) U.S. Cl.
CPC ............ *A61F 5/026* (2013.01); *A61F 5/0102* (2013.01); *A61F 2005/0158* (2013.01); *A61F 2005/0167* (2013.01)

(58) Field of Classification Search
CPC ........ A61F 5/01; A61F 5/0102; A61F 5/0118; A61F 5/013; A61F 5/02; A61F 5/022; A61F 5/026; A61F 5/058; A61F 5/05858; A61F 5/37; A61F 5/3715; A61F 5/3723; A61F 5/3753; A61F 2005/0132; A61F 2005/0144; A61F 2005/0146; A61F 2005/0151; A61F 2005/0153; A61F 2005/0158; A61F 2005/0165; A61F 2005/0167; A61F 5/024; A41F 3/02; A61G 13/125; A61M 1/3633
See application file for complete search history.

(56) References Cited

U.S. PATENT DOCUMENTS

| | | |
|---|---|---|
| 5,018,513 A | 5/1991 | Charles |
| 5,188,587 A | 2/1993 | McGuire et al. |
| 5,385,536 A * | 1/1995 | Burkhead ............. A61F 5/3753 602/5 |
| 5,407,420 A | 4/1995 | Bastyr et al. |
| 5,665,058 A * | 9/1997 | Young .................. A61F 5/3753 602/20 |
| 6,106,493 A | 8/2000 | Rozell |
| 7,255,679 B2 | 8/2007 | Kania et al. |
| 8,556,840 B2 | 10/2013 | Burke et al. |
| 9,320,635 B2 | 4/2016 | Ex-Lubeskie et al. |
| 10,085,875 B2 | 10/2018 | Fair et al. |
| 10,285,841 B2 | 5/2019 | Pappady |
| 10,327,942 B2 | 6/2019 | Nolt et al. |
| 10,786,384 B2 | 9/2020 | Nakamitsu |
| 2002/0153401 A1 | 10/2002 | Werling |

(Continued)

*Primary Examiner* — Ophelia A Hawthorne
*Assistant Examiner* — Gina McCarthy
(74) *Attorney, Agent, or Firm* — Olav M. Underdal; IDP Patent Services

(57) ABSTRACT

A shoulder brace device includes: a torso band, an arm band, and a brace mechanism, such that the brace mechanism is configured to connect to the torso band and the arm band; wherein the brace mechanism includes a ball joint assembly, such that the shoulder brace device enables free range of movement; wherein the brace mechanism can be locked in place or tightened for reduced range of movement.

22 Claims, 8 Drawing Sheets

Shoulder Brace Device

(56) References Cited

U.S. PATENT DOCUMENTS

| | | | |
|---|---|---|---|
| 2011/0125242 A1* | 5/2011 | Zahler | A61F 5/3715 |
| | | | 607/149 |
| 2014/0058304 A1 | 2/2014 | Ex-Lubeskie et al. | |
| 2014/0101851 A1* | 4/2014 | Schuerch, Jr. | A61G 13/125 |
| | | | 5/624 |
| 2016/0213079 A1* | 7/2016 | Amsler, Jr. | A41F 3/02 |
| 2017/0065450 A1 | 3/2017 | Pappady | |
| 2019/0117433 A1* | 4/2019 | Sacco | A61F 5/024 |
| 2020/0078200 A1* | 3/2020 | Hardt | A61F 5/013 |
| 2021/0038417 A1 | 2/2021 | Marti | |
| 2021/0038421 A1 | 2/2021 | Marti | |
| 2021/0346651 A1* | 11/2021 | Lerner | A61M 1/3633 |

* cited by examiner

Shoulder Brace Device

Shoulder Brace Device

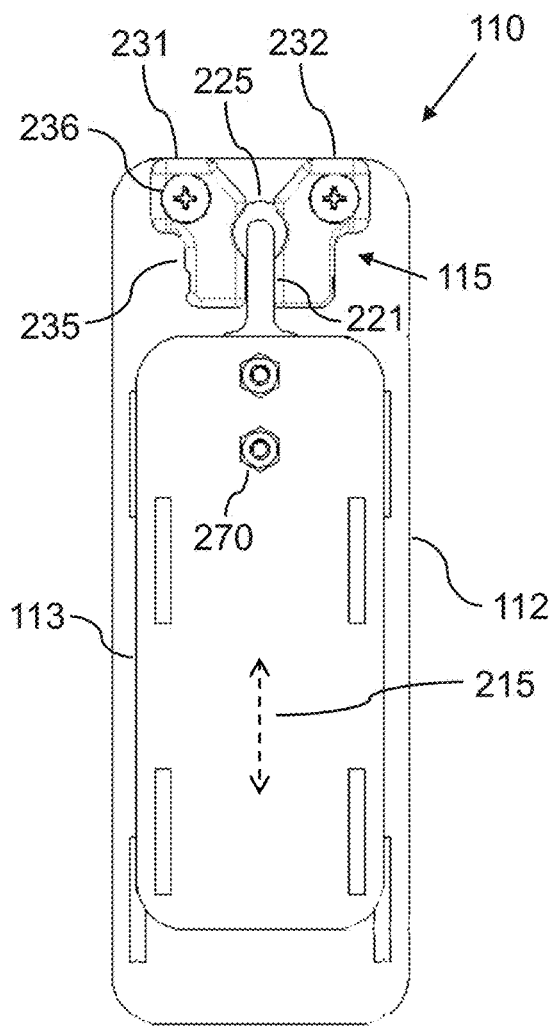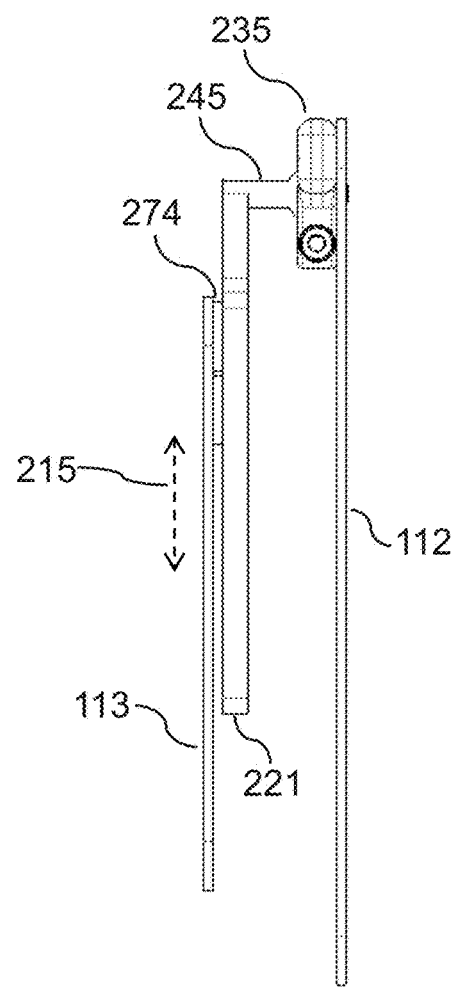

SHOULDER BRACE DEVICE

CROSS-REFERENCE TO RELATED APPLICATIONS

N/A.

FIELD OF THE INVENTION

The present invention relates generally to the field of medical braces, and more particularly to methods and systems for shoulder braces with controlled range of motion.

BACKGROUND OF THE INVENTION

When a shoulder is injured and healing, abrupt stops of motion are a main cause of discomfort and pose a risk of further injury. In the first few weeks of healing post-surgery, shoulders should not move to avoid unnecessary pain and discomfort while also protecting the shoulder. In the next 2-3 months, the shoulder should begin to stretch and have regulated movement in comfortable positions. And finally, the shoulder should be conditioned post therapy by applying a loaded force for the shoulder to work and strengthen against. However, shoulder braces currently available in general cannot prevent movement or control movement of the shoulder, and are also incapable of providing assistance in the conditioning and strengthening of the shoulder.

As such, considering the foregoing, it may be appreciated that there continues to be a need for novel and improved devices and methods for shoulder brace devices.

SUMMARY OF THE INVENTION

The foregoing needs are met, to a great extent, by the present invention, wherein in aspects of this invention, enhancements are provided to the existing model of shoulder brace devices.

In an aspect, a shoulder brace device can include:
a) a torso band;
b) an arm band; and
c) a brace mechanism, which can include:
  i. a main plate, which can be configured to connect to the torso band; and
  ii. an arm plate, which can be configured to connect the arm band;
such that the brace mechanism can be positioned between an arm and a body of a user, wherein the main plate and the arm plate can be rotatably connected;
such that the brace mechanism can enable free range of movement of the arm, such that the user can move their arm to adjust the brace mechanism to a comfortable position;
such that the brace mechanism can be configured to be lockable in the comfortable position to prevent injuring motions to a healing shoulder.

In a related aspect, the brace mechanism can include:
a) a ball joint assembly, which can include:
  i. a ball joint arm, which can be connected to the arm plate, wherein the ball joint arm can include a ball that is offset perpendicularly from an end of the ball joint arm; and
  ii. a ball joint mounter, which can be attached to the main plate, such that the ball joint mounter can be configured to receive the ball of the ball joint arm, such that the ball joint arm can be secured and freely rotatable within the ball joint mounter;
wherein the ball joint assembly can enable the arm plate to freely rotate with respect to the main plate.

In a further related aspect, the brace mechanism can further include:
a) an adjustment assembly, which can include:
  i. a screw, which can be insertable through lower ends of the left mounting piece and the right mounting piece; and
  ii. an adjustment knob, which can include a twisting structure, such that the twisting structure can be configured to twist the screw;
such that when the screw is twisted clockwise by the adjustment knob, the screw can move the left mounting piece closer to the right mounting piece, such that friction force around the ball in the ball shaped chamber can increase;
such that when the screw is twisted counterclockwise by the adjustment knob, the screw can move the left mounting piece further from the right mounting piece, such that the friction force around the ball in the ball shapes chamber can decrease;
such that the adjustment assembly can be completely loosened to allow for free range of movement, such that the adjustment assembly can be completely tightened to lock the ball joint arm in the comfortable position;
such that the adjustment assembly can be gradually loosened or tightened to lower or increase range of movement.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 3A is front view of a brace mechanism, according to an embodiment of the invention.

FIG. 3B is right view of a brace mechanism, according to an embodiment of the invention.

DETAILED DESCRIPTION

Figure 1A:
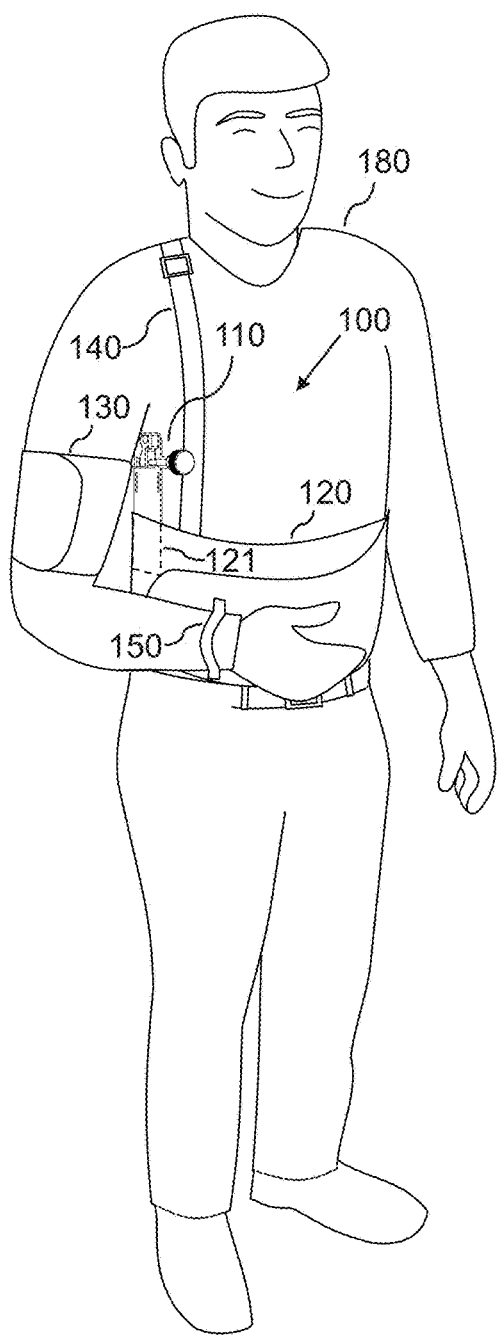
FIG. 1A is an illustration of a user wearing the shoulder brace device, according to an embodiment of the invention.

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In the following, we describe the structure of an embodiment of a shoulder brace device 100 with reference to FIG. 1A, in such manner that like reference numerals refer to like components throughout; a convention that we shall employ for the remainder of this specification.

Figure 1B:
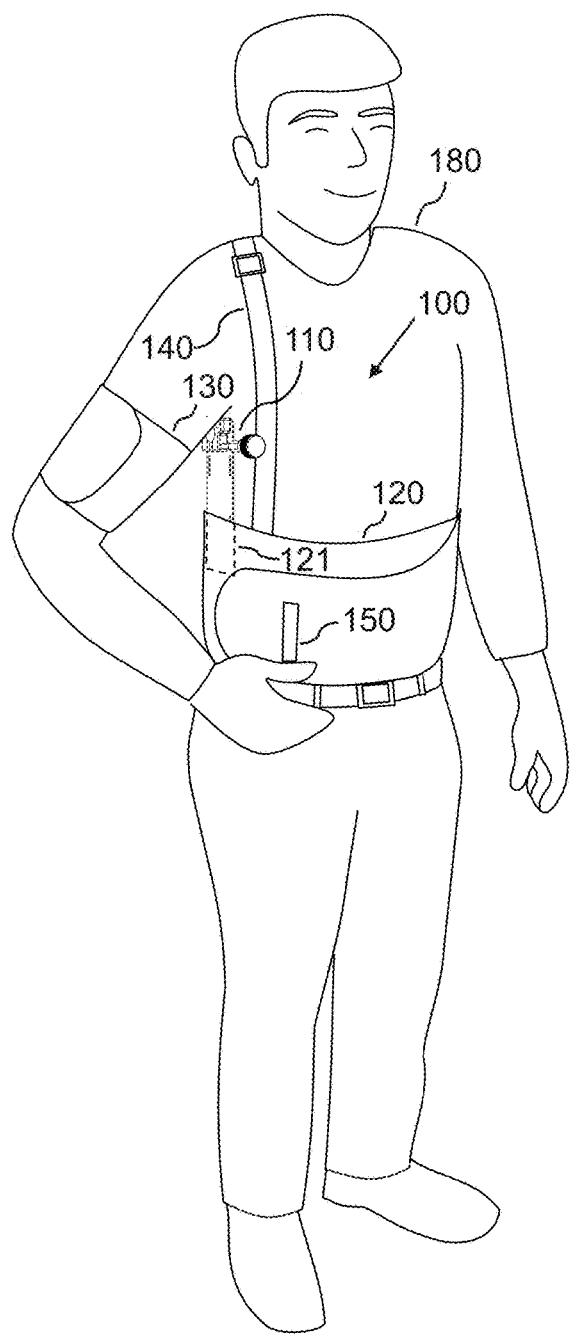
FIG. 1B is an illustration of a user wearing the shoulder brace device in an alternate position, according to an embodiment of the invention.
Figure 1C:
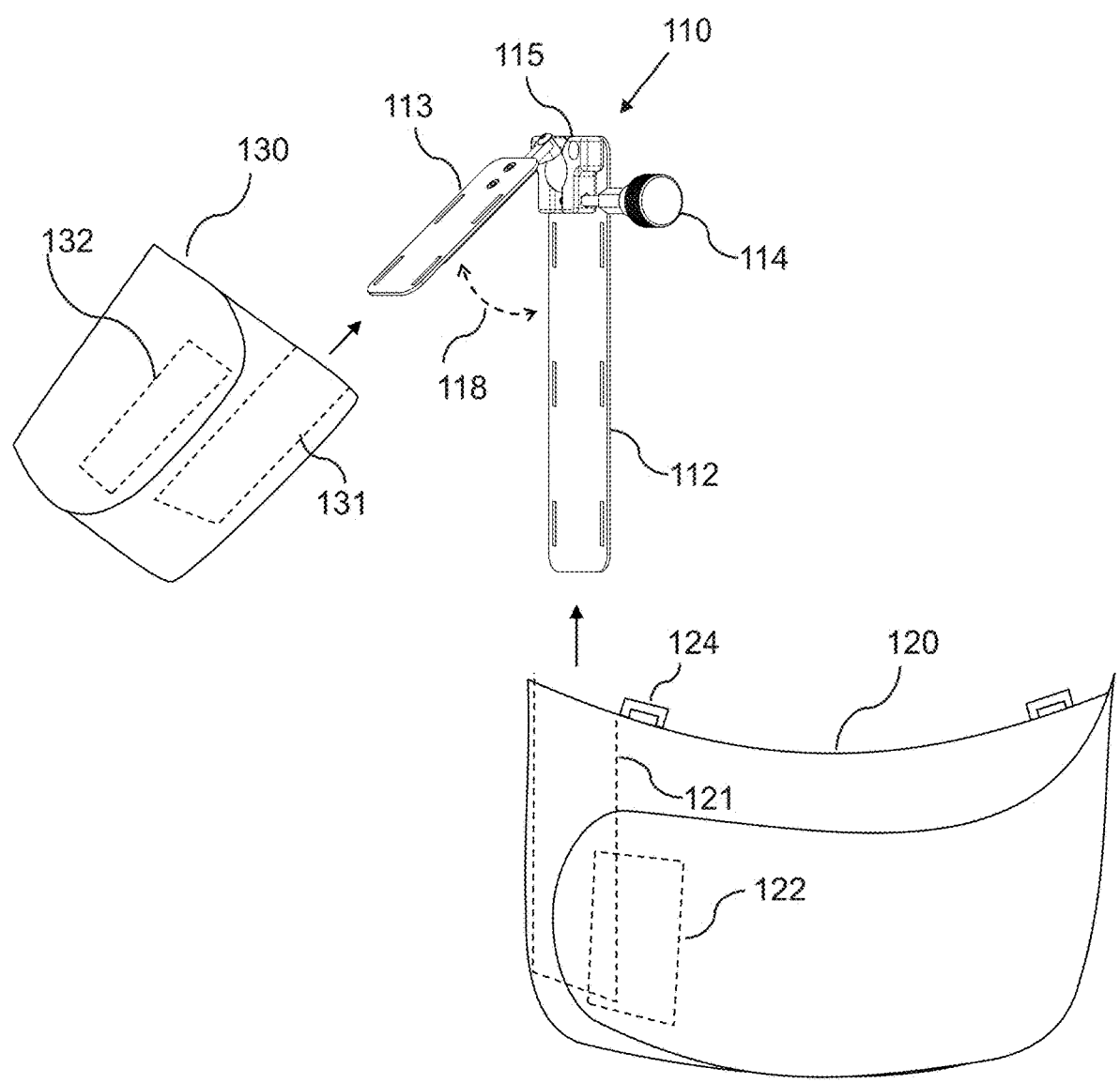
FIG. 1C is a front view of an exploded shoulder brace device, according to an embodiment of the invention.

In an embodiment, as shown in FIGS. 1A, 1B, and 1C, a shoulder brace device 100 can include:
a) a torso band 120, which can also be referred to as a torso attachment 120;
b) an arm band 130, which can also be referred to as an arm attachment 130; and
c) a brace mechanism 110, which can include:
  i. a main plate 112, which can also be referred to as a torso connector portion 112, which can be configured to connect to the torso band 120; and
  ii. an arm plate 113, which can also be referred to as an arm connector portion 113, which can be configured to connect to the arm band 130;
such that the brace mechanism 110 can be positioned between an arm and a body of a user 180, wherein the main plate 112 and the arm plate 113 can be pivotably 118 connected;
such that the brace mechanism 110 can allow free range of movement of the arm, such that the user 180 can move their arm to adjust the brace mechanism 110 to a comfortable position;
such that the brace mechanism 110 can be configured to be lockable in the comfortable position to prevent injuring motions to a healing shoulder.

In a related embodiment, as shown in FIGS. 1C, 5A, 5B, 6A, and 6B, the torso band 120 can include:
a) at least one torso pocket 121, such that the at least one torso pocket 121 can be configured to receive the main plate 112; and
wherein the arm band 130 can include:
b) at least one arm pocket 131, such that the at least one arm pocket 131 can be configured to receive the arm plate 113;
such that the brace mechanism 110 can be configured to be insertable into the arm band 130 and the torso band 120;
wherein the at least one torso pocket 121 and the at least one arm pocket 131 can be sewn externally or internally into the torso band 120 and the arm band 130, respectively.

In a further related embodiment, as shown in FIGS. 1C, 5A, 5B, 6A and 6B, the torso band 120 can include:
a) a right torso pocket 121, which can be positioned to align with a right arm of the user 180 when the user 180 is wearing the torso band 120, such that the right torso pocket 121 can be configured to receive the main plate 112; and
b) a left torso pocket 121, which can be positioned to align with a left arm of the user 180 when the user 180 is wearing the torso band 120, such that the left torso pocket 121 can be configured to receive the main plate 112;
such that the brace mechanism 110 can be usable on the left and the right arm of the user 180.

In another related embodiment, as shown in FIGS. 2A, 2B, 3A, and 3B, the brace mechanism 110 can include:
a) a ball joint assembly 115, which can include:
  i. a ball joint arm 220, which can be connected to the arm plate 113, wherein the ball joint arm 221 can include a ball 225 that is offset perpendicularly from an end of the ball joint arm 221;
  ii. a ball joint mounter 230, which can be attached to the main plate 112, such that the ball joint mounter 230 can be configured to receive the ball 225 of the ball joint arm 221, such that the ball joint arm 221 can be secured and freely rotatable within the ball joint mounter 230; and
  iii. mounting screws 238, which can be inserted through the ball joint mounter 230 and screwed into the main plate 112, such that the mounting screws 238 can attach the ball joint mounter 230 to the main plate 112;
wherein the ball joint assembly 115 can enable the arm plate 113 to freely rotate (in the XYZ directions) with respect to the main plate 112, as shown in FIGS. 4A, 4B, 4C, and 4D.

Figure 2A:
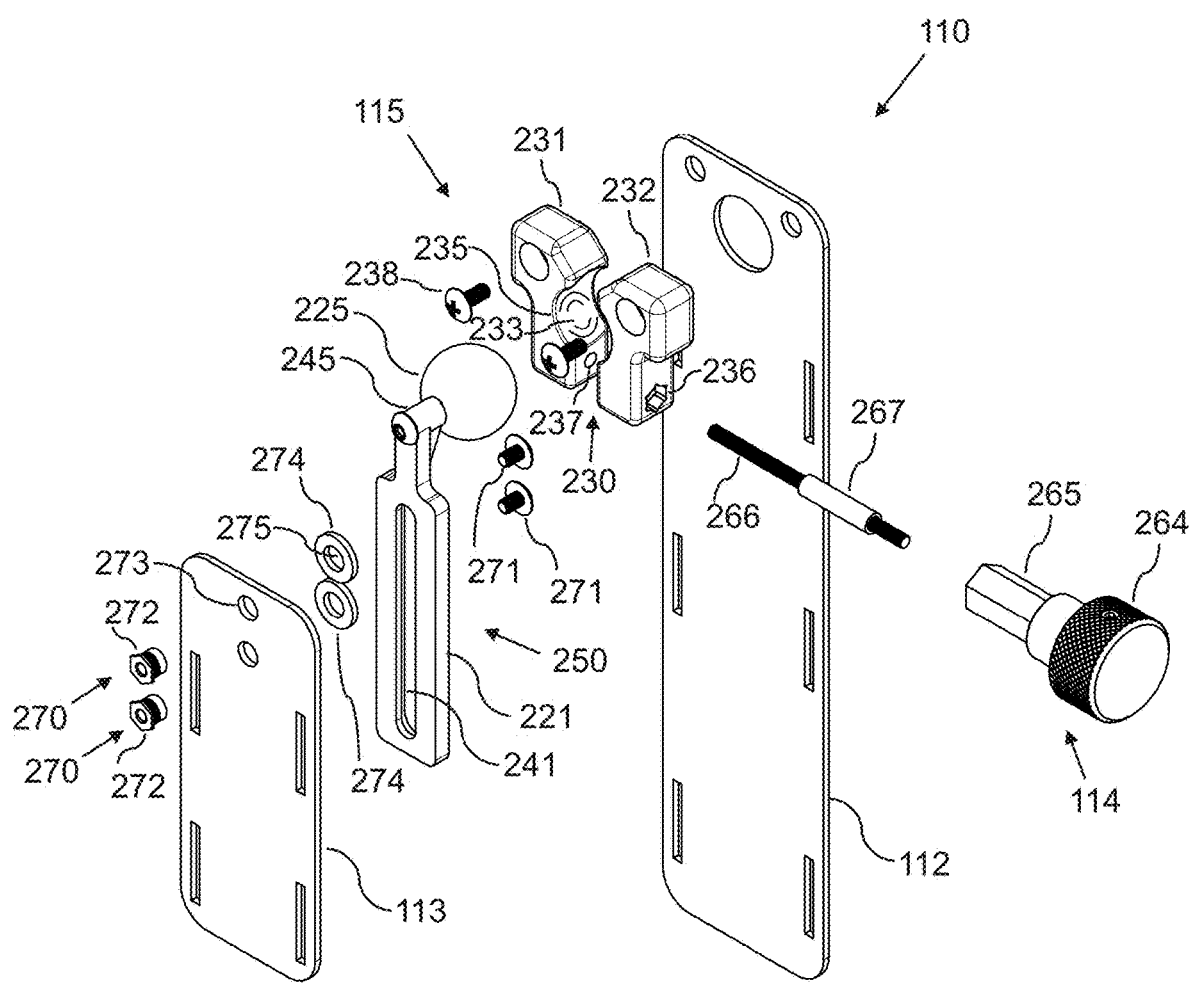
FIG. 2A is a perspective exploded view of a brace mechanism, according to an embodiment of the invention.
Figure 2B:
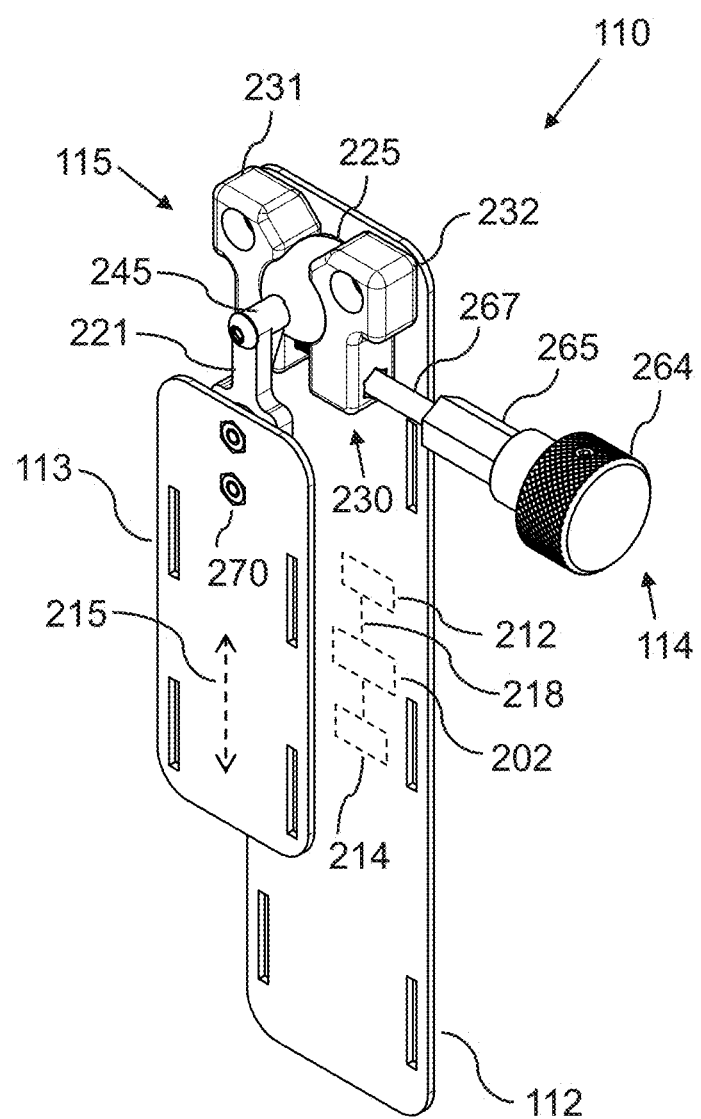
FIG. 2B is a perspective view of a brace mechanism, according to an embodiment of the invention.
Figure 4A:
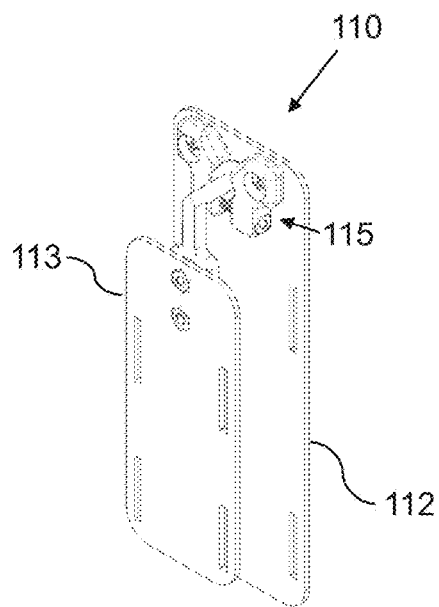
FIG. 4A is perspective view of a brace mechanism in a chosen comfortable position, according to an embodiment of the invention.
Figure 4B:
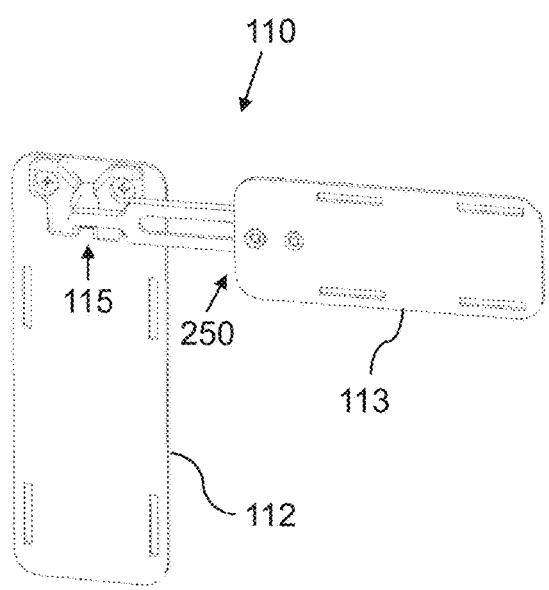
FIG. 4B is perspective view of a brace mechanism in a chosen comfortable position, according to an embodiment of the invention.
Figure 4C:
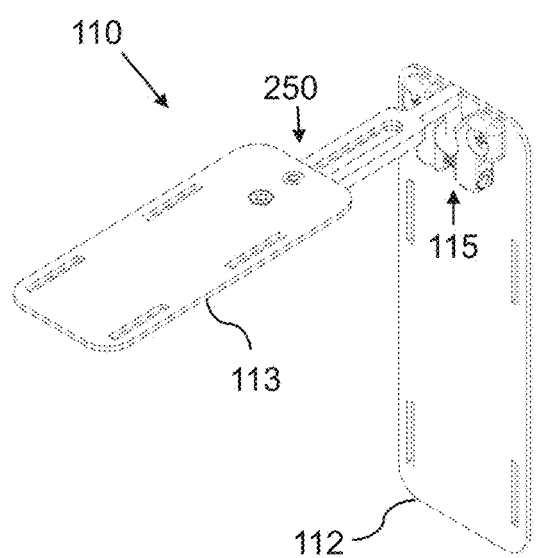
FIG. 4C is perspective view of a brace mechanism in a chosen comfortable position, according to an embodiment of the invention.
Figure 4D:
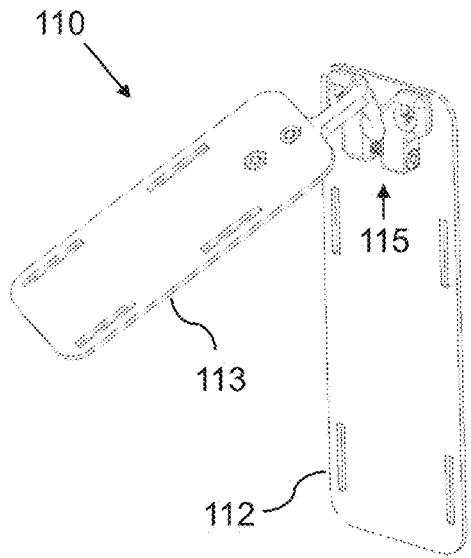
FIG. 4D is perspective view of a brace mechanism in a chosen comfortable position, according to an embodiment of the invention.

In a related embodiment, as shown in FIGS. 2A, 2B and 3B, the ball joint arm 221 can include:
a) an offset piece 245, which can be perpendicularly attached to the end of the ball joint arm 221, such that the offset piece 245 can attach the ball 225 to the ball joint arm 221, such that the offset piece 245 can perpendicularly offset the ball 225 in respect to the ball joint arm 221.

In another related embodiment, as shown in FIGS. 2A, 2B, and 3A, the ball joint mounter 230 can include:
 a) a left mounting piece 231, which can include a spherically curved concave right inner surface 233; and
 b) a right mounting piece 232, which can include a spherically curved concave left inner surface;
 such that the left mounting piece 231 and the right mounting piece 232 can be positioned on a left and a right side of the ball 225, respectively, such that the left mounting piece 231 and the right mounting piece 232 can form a ball shaped chamber 235 around the ball 225.

In a related embodiment, as shown in FIGS. 2A and 2B, the brace mechanism 110 can further include:
 a) an adjustment assembly 114, which can include:
  i. a screw 266, which can be insertable through protruding apertures 236, 237 in lower ends of the left mounting piece 231 and the right mounting piece 232, such that the screw 266 can extend past a right end of the right mounting piece 232; and
  ii. an adjustment knob 264, which is connected to an outer end of the screw 266, such that the adjustment knob enables adjustment of the screw via a rotation of the adjustment knob;
 for example via a knob body 265, such that the knob body 265 can screw onto the screw 266 on the right end of the right mounting piece 232;
 such that when the screw 266 is turned clockwise by the adjustment knob 264, the screw 266 can move the left mounting piece 231 closer to the right mounting piece 232, such that friction force around the ball 225 in the ball shaped chamber 235 can increase;
 such that when the screw 266 is turned counterclockwise by the adjustment knob 264, the screw 266 can move the left mounting piece 231 further from the right mounting piece 232, such that the friction force around the ball 225 in the ball shaped chamber 235 can decrease;
 such that the ball joint assembly 115 can be completely loosened to allow for free range of movement, such that the ball joint assembly 115 can be completely tightened to lock the brace mechanism 110 in the comfortable position;
 such that the ball joint assembly 115 can be gradually loosened or tightened to lower or increase range of movement.

In a further related embodiment, the screw 267 can protrude through the protruding aperture 236 of the right mounting piece 232, such that the screw 267 screws into a threaded aperture 237 of the left mounting piece 231, such that when the screw 267 is screwed clockwise a screw body 267 impacts with the right mounting piece 232 and thereby moves the left mounting piece 231 closer to the right mounting piece 232, such that friction force around the ball 225 in the ball shaped chamber 235 can increase.

In another further related embodiment, as shown in FIGS. 2A, 2B, 4B and 4C, the arm plate 113 can be slidably attached to the ball joint arm 221, such that when the arm of the user 180 is lifted laterally, the arm plate 113 can slide with respect to the ball joint assembly 115 to provide the necessary extension for the arm of the user 180 to extend.

In a related embodiment, as shown in FIGS. 2A, 2B, 4B and 4C, the brace mechanism 110 can further include at least one slider assembly 270, which can include two bolt assemblies 270, wherein the at least one slider assembly 270 can include:
 a) a bolt 271, which can include a threaded portion;
 b) a nut 272, which is attachable to the bolt 271; and
 c) a sliding spacer 274, which comprises a central aperture 275, such that the slider spacer 274 is mounted between the arm plate 113 and the ball joint arm 221, with the threaded portion of the bolt 271 protruding through the central aperture 275;
 wherein the ball joint arm 221 can further include an elongated opening 241;
 wherein the arm plate 113 can further include at least one plate aperture 273;
 such that the threaded portion of the bolt 271 can be inserted through the elongated opening 241 and the plate aperture 273, such that the slider assembly 270 is secured with the bolt 271 attached to an outer end of the threaded portion;
 such that the slider spacer 274 enables a smooth sliding motion 215 of the arm plate along the elongated opening 241;
 such that the slider assembly 270 enables the arm plate to slide along the elongated opening 241 when the user 180 lifts or extends the arm.

Thus, in related embodiments, the brace mechanism can include a ball joint at the arm pit location to allow for movement in all directions, and a sliding system at the arm plate to allow for the extension of the arm. The tension in the ball join can be adjusted to have the following:
 a) free movement;
 b) movement with load to overcome friction on the ball joint; or
 c) locked position;
 wherein, when the arm is lifted laterally, the arm plate slides 215 with respect to the ball joint assembly to provide the necessary extension.

In another related embodiment, as shown in FIGS. 1A, 1B and 1C, the shoulder brace device 100 can further include:
 a) a suspender 140, which can hold up the torso band 120;
 wherein the torso band 120 can include a front suspender attachment clip 124 and a back suspender attachment clip 124, which are positioned around an upper side of the torso band 120, such that the suspender 140 can be mounted over a shoulder of the user 180 and can attach to the front suspender attachment clip 124 and the back suspender attachment clip 124 on a front and a back side, respectively, of the torso of the user 180 to hold up the torso band 120.

Figure 5A:
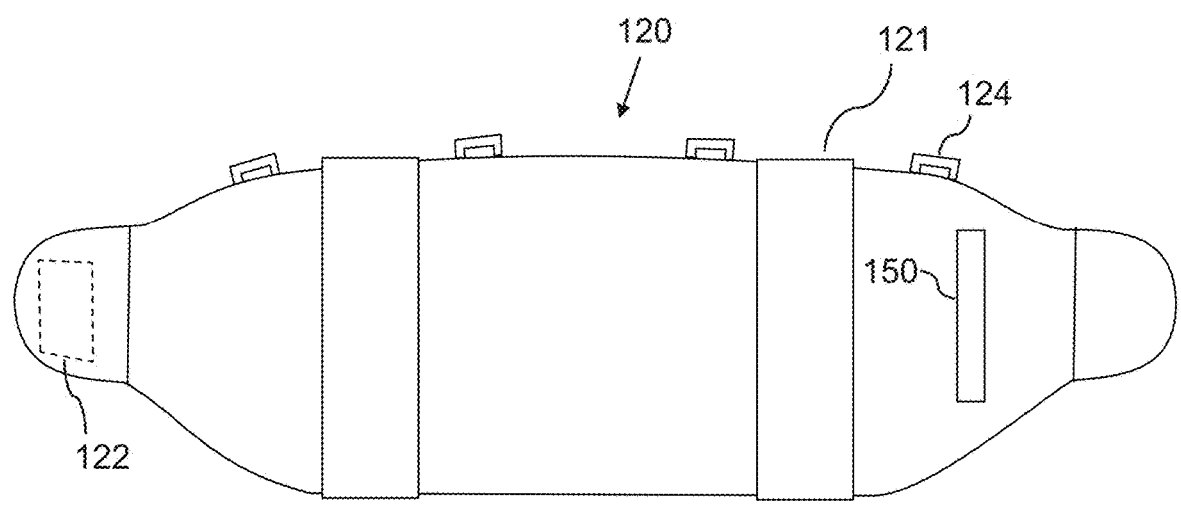
FIG. 5A is front view of a torso band, according to an embodiment of the invention.
Figure 5B:
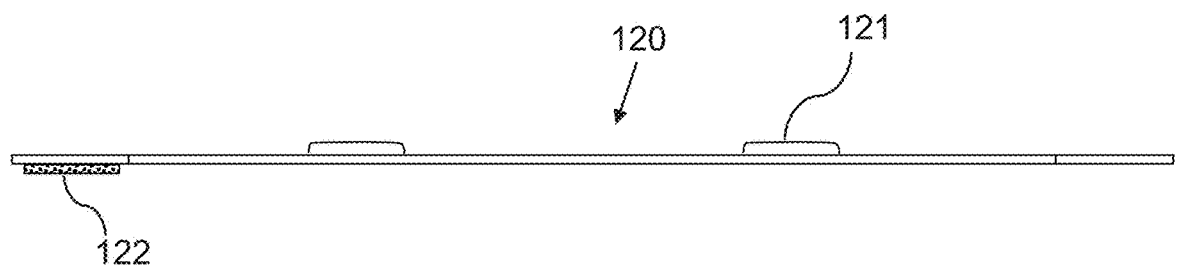
FIG. 5B is top view of a torso band, according to an embodiment of the invention.

In another related embodiment, as shown in FIGS. 1C and 5A, an outer end of the torso band 120 can include a torso attachment structure 122, such that the torso attachment structure 122 can attach to the torso band 120 when the torso band 120 is wrapped around the torso of the user 180, such that the torso band 120 can be adjustably securable around the torso of the user 180.

In a further related embodiment, the torso attachment structure 122 can be a hook and loop fastener, buttons, snap-in buttons, or other types of fastener.

Figure 6A:
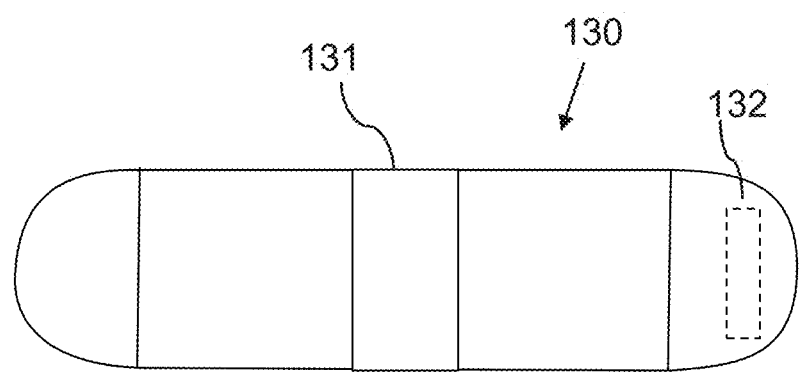
FIG. 6A is front view of an arm band, according to an embodiment of the invention.
Figure 6B:
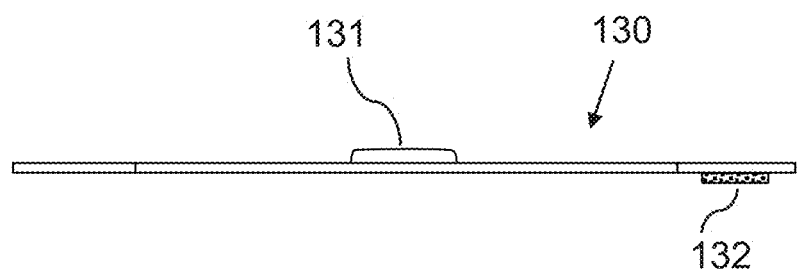
FIG. 6B is top view of an arm band, according to an embodiment of the invention.

In yet another related embodiment, as shown in FIGS. 1C and 6A, an outer end the arm band 130 can include an arm attachment structure 132, such that the arm attachment structure 132 can attach to the arm band 130 when wrapped around the arm of the user 180, such that the arm band 130 can be adjustably securable around the arm of the user 180;

In a further related embodiment, the arm attachment structure 132 can be a hook and loop fastener, buttons, snap-in buttons, or other types of fastener.

In another related embodiment, as shown in FIGS. 1A, 1B and 5A, the torso band 120 can include a strap 150 to hold a wrist of the user 180 in position, such that the wrist can be insertable through the strap 150, wherein the strap 150 can be elastic.

Thus, in various related embodiment, the shoulder brace device 100 can function as a high-quality shoulder brace that protects against abrupt stops of motion which is a major cause of discomfort and risk of injury. The shoulder brace device 100 can be used during post-surgery, physiotherapy, and strengthening phases for up to 12 months. The shoulder brace device 100 can enable lock position and controlled movement range by the user, and can be worn under or over clothing. The user can wear and operate the shoulder brace device 100 without assistance. The top priorities of the shoulder brace device are protection of the shoulder, comfort, high-quality breathable material, and easy to use. The shoulder brace device 100 can be designed to be lightweight and compact.

The shoulder brace device 100 can be intended to serve in three phases:
a) First few weeks post-surgery—Lock the position of the shoulder and prevent the shoulder from moving intentionally or accidentally. (This will avoid unnecessary pain and discomfort while protecting the shoulder);
b) Next 2-3 months of physiotherapy—the shoulder brace device 100 will help with the stretching of the shoulder in the early phases and to hold the arm at a certain position during the therapy. The loaded force will prevent sudden movement and stops of the arm; and
c) Conditioning (post therapy)—the shoulder brace device 100 will assist with strengthening the shoulder muscle by applying friction loaded force.

Thus, in an embodiment, as shown in FIGS. 1A, 1B, and 1C, a shoulder brace device 100, can include:
a) a torso attachment 120, which is configured to be attached to a torso of a user;
b) an arm attachment 130, which is configured to be attached to an arm of the user; and
c) a brace mechanism 110, which can include:
a torso connector portion 112, which is configured to connect to the torso attachment 120; and
an arm connector portion 113, which is configured to connect to the arm attachment 130;
wherein the torso connector portion 112 and the arm connector portion 113 can be rotatably connected;
such that the brace mechanism 110 is positionable between the arm and the torso of the user;
such that the brace mechanism 110 can enable free range of movement of the arm, such that the user 180 can move their arm to adjust the brace mechanism 110 to a comfortable position;
such that the brace mechanism 110 can be configured to be lockable in the comfortable position to prevent injuring motions to a healing shoulder.

In various related embodiments, the shoulder brace device 100 can be far less obtrusive than traditional splints and may even be used under a dress shirt.

In related embodiments, the torso and arm attachments 120, 130 can be made from neoprene and/or breathable or weather adjusting fabrics, and can be nano-coated to ensure that sweat and dirt is repelled. Thereby the shoulder brace device 100, can be worn during recreational activities, such as golfing and skiing; at work; or in the home, such as even while sleeping.

In a related embodiment, as shown in FIG. 2B, the shoulder brace device 100 can further include:
a) at least one sensor 212, which can include:
i. an accelerometer, for measuring movement and/or acceleration;
ii. a pivot angle sensor for measuring a pivot angle of the shoulder brace device 100; and
iii. a friction sensor for measuring a resistance setting of the shoulder brace device 100;
b) a processor 202, which can be a system-on-chip microcontroller; and
c) a wireless transmitter 214, which can be a BLUETOOTH™ transceiver or transmitter; all connected via
d) a data bus 218;
such that the shoulder brace device 100 can continuously transmit patient data to doctors and therapists to access via mobile devices or websites, to allow for measurement of progress and adjustment of the shoulder brace device 100, wherein the doctors and therapists can provides the patient user with the recommended settings of the shoulder brace device 100, whereby the shoulder brace device 100 allows patient and medical practitioner/doctor/therapist to continuously collaborate to ensure optimal recovery and rehabilitation.

Here has thus been described a multitude of embodiments of the shoulder brace device 100 and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent and should be considered fully included in this specification and the claims appended hereto. Accordingly, since numerous modifications and variations will readily occur to those skilled in the art, the invention is not limited to the exact construction and operation illustrated and described, and thus, all suitable modifications and equivalents may be resorted to, falling within the scope of the invention.

What is claimed is:
1. A shoulder brace device, comprising:
a) a torso band, which is configured to be positioned around a torso of a user;
b) an arm band, which is configured to be positioned around an arm of the user; and
c) a brace mechanism, comprising:
a main plate, which is configured to connect to the torso band;
an arm plate, which is configured to connect to the arm band; and
a ball joint assembly, which comprises:
a ball joint arm, which is connected to the arm plate, such that the ball joint arm comprises a ball that is offset perpendicularly from an end of the ball joint arm; and
a ball joint mounter, which is attached to the main plate, such that the ball joint mounter is configured to receive the ball of the ball joint arm, such that the ball joint arm is secured and freely rotatable within the ball joint mounter;
wherein the ball joint assembly enables the arm plate to freely rotate with respect to the main plate;
wherein the arm plate is slidably attached to the ball joint arm, such that when the arm of the user is lifted laterally, the arm plate slides with respect to the ball joint assembly to provide a necessary extension for the arm of the user to extend;

wherein the brace mechanism further comprises at least one slider assembly, which comprises:
a bolt, which comprises a threaded portion; and
a nut, which is attachable to the bolt;

wherein the ball joint arm further comprises an elongated opening wherein the arm plate further comprises a plate aperture;

such that the threaded portion of the bolt is inserted through the elongated opening of the ball joint arm and the plate aperture, such that the at least one slider assembly is secured with the bolt attached to an outer end of the threaded portion;

such that the at least one slider assembly enables the arm plate to slide along the elongated opening when the user lifts or extends the arm;

wherein an upper end of the main plate and an upper end of the arm plate are pivotably connected, such that the brace mechanism is configured to be positionable between the arm and the torso of the user;

wherein the torso band comprises:
at least one torso pocket, such that the at least one torso pocket is configured to receive the main plate; and wherein the arm band comprises:
at least one arm pocket, such that the at least one arm pocket is configured to receive the arm plate;

such that the brace mechanism is configured to be insertable into the arm band and the torso band;

such that a lower end of the main plate projects vertically downward into the at least one torso pocket, when the shoulder brace device is mounted on the user;

such that the brace mechanism allows movement of the arm, such that the user is enabled to move the arm to adjust the brace mechanism to a comfortable position;

such that the brace mechanism is configured to be lockable in the comfortable position to prevent injuring motions to a healing shoulder.

2. The shoulder brace device of claim 1, wherein the ball joint mounter comprises:
a) a left mounting piece, which comprises a spherically curved right inner surface; and
b) a right mounting piece, which comprises a spherically curved left inner surface;

such that the left mounting piece and the right mounting piece are positioned on a left and a right side of the ball, respectively, such that the left mounting piece and the right mounting piece form a ball shaped chamber around the ball.

3. The shoulder brace device of claim 2, wherein the brace mechanism further comprises an adjustment assembly, which comprises:
a) a screw, which is insertable through lower ends of the left mounting piece and the right mounting piece, such that the screw extends past a right end of the right mounting piece; and
b) an adjustment knob, which is connected to an outer end of the screw, such that the adjustment knob enables adjustment of the screw via a rotation of the adjustment knob;

such that when the screw is turned clockwise by the adjustment knob, the screw moves the left mounting piece closer to the right mounting piece, such that a friction force around the ball in the ball shaped chamber increases;

such that when the screw is turned counterclockwise by the adjustment knob, the screw moves the left mounting piece further from the right mounting piece, such that the friction force around the ball in the ball shaped chamber decreases;

such that the ball joint assembly is tightened to lock the ball joint arm in the comfortable position.

4. The shoulder brace device of claim 1, wherein the torso band comprises:
a) a right torso pocket, which is positioned to align with a right arm of the user when the user is wearing the torso band, such that the right torso pocket is configured to receive the main plate; and
b) a left torso pocket, which is positioned to align with a left arm of the user when the user is wearing the torso band, such that the left torso pocket is configured to receive the main plate;

such that the brace mechanism is usable on the left arm and the right arm of the user.

5. The shoulder brace device of claim 1, wherein the ball joint arm comprises:
an offset piece, which is perpendicularly attached to the end of the ball joint arm, such that the offset piece attaches the ball to the ball joint arm, such that the offset piece perpendicularly offsets the ball in respect to the ball joint arm.

6. The shoulder brace device of claim 1, wherein the at least one slider assembly further comprises:
a slider spacer, which comprises a central aperture, such that the slider spacer is mounted between the arm plate and the ball joint arm, with the threaded portion of the bolt protruding through the central aperture;

such that the slider spacer enables a smooth sliding motion of the arm plate along the elongated opening.

7. The shoulder brace device of claim 1, wherein the shoulder brace device further includes:
a suspender, which holds up the torso band;

wherein the torso band comprises a front suspender attachment clip and a back suspender attachment clip, which are positioned around an upper side of the torso band, such that the suspender is mountable over a shoulder of the user, such that the suspender is attachable to the front suspender attachment clip and the back suspender attachment clip on a front and a back side, respectively, of the torso of the user, to hold up the torso band.

8. The shoulder brace device of claim 1, wherein an outer end of the torso band comprises a torso attachment structure, such that the torso attachment structure is configured to attach to the torso band when the torso band is wrapped around the torso of the user, such that the torso band is adjustably securable around the torso of the user.

9. The shoulder brace device of claim 1, wherein an outer end of the arm band comprises arm attachment structure, such that the arm attachment structure is configured to attach to the arm band when the arm band is wrapped around the arm of the user, such that the arm band is adjustably securable around the arm of the user.

10. The shoulder brace device of claim 1, wherein the torso band further comprises a strap to hold a wrist of the user in position, such that the wrist is insertable through the strap.

11. A shoulder brace device, comprising:
a) a torso attachment, which is configured to be attached to a torso of a user;
b) an arm attachment, which is configured to be attached to an arm of the user; and
c) a brace mechanism, comprising:
  a torso connector portion, which is configured to connect to the torso attachment;
  an arm connector portion, which is configured to connect to the arm attachment; and
  a ball joint assembly, which comprises:
    a ball joint arm, which is connected to the arm connector portion, such that the ball joint arm comprises a ball that is offset perpendicularly from an end of the ball joint arm; and
    a ball joint mounter, which is attached to the torso connector portion, such that the ball joint mounter is configured to receive the ball of the ball joint arm, such that the ball joint arm is secured and freely rotatable within the ball joint mounter;
  wherein the ball joint assembly enables the arm connector portion to freely rotate with respect to the torso connector portion;
  wherein the arm connector portion is slidably attached to the ball joint arm, such that when the arm of the user is lifted laterally, the arm connector portion slides with respect to the ball joint assembly to provide a necessary extension for the arm of the user to extend;
  wherein an upper end of the torso connector portion and an upper end of the arm connector portion are pivotably connected, such that the brace mechanism is configured to be positionable between the arm and the torso of the user;
wherein the torso band comprises:
  at least one torso pocket, such that the at least one torso pocket is configured to receive the torso connector portion; and
wherein the arm band comprises:
  at least one arm pocket, such that the at least one arm pocket is configured to receive the arm connector portion;
  such that the brace mechanism is configured to be insertable into the arm band and the torso band;
  such that a lower end of the torso connector portion projects vertically downward into the at least one torso pocket, when the shoulder brace device is mounted on the user:
  such that the brace mechanism allows movement of the arm, such that the user is enabled to move the arm to adjust the brace mechanism to a comfortable position;
  such that the brace mechanism is configured to be lockable in the comfortable position to prevent injuring motions to a healing shoulder.

12. The shoulder brace device of claim 11, wherein the ball joint mounter comprises:
a) a left mounting piece, which comprises a spherically curved right inner surface; and
b) a right mounting piece, which comprises a spherically curved left inner surface;
such that the left mounting piece and the right mounting piece are positioned on a left and a right side of the ball, respectively, such that the left mounting piece and the right mounting piece form a ball shaped chamber around the ball.

13. The shoulder brace device of claim 12, wherein the brace mechanism further comprises an adjustment assembly, which comprises:
a) a screw, which is insertable through lower ends of the left mounting piece and the right mounting piece, such that the screw extends past a right end of the right mounting piece; and
b) an adjustment knob, which is connected to an outer end of the screw, such that the adjustment knob enables adjustment of the screw via a rotation of the adjustment knob;
such that when the screw is turned clockwise by the adjustment knob, the screw moves the left mounting piece closer to the right mounting piece, such that a friction force around the ball in the ball shaped chamber increases;
such that when the screw is turned counterclockwise by the adjustment knob, the screw moves the left mounting piece further from the right mounting piece, such that the friction force around the ball in the ball shaped chamber decreases;
such that the ball joint assembly is tightened to lock the ball joint arm in the comfortable position.

14. The shoulder brace device of claim 11, wherein the brace mechanism further comprises a slider assembly, which comprises:
a) the ball joint arm, which comprises an elongated opening; and
b) at least one bolt assembly, comprising:
  a bolt, which comprises a threaded portion; and
  a nut, which is attachable to the bolt;
  wherein the arm connector portion further comprises a plate aperture;
such that the threaded portion of the bolt is inserted through the elongated opening of the ball joint arm and the plate aperture, such that the slider assembly is secured with the bolt attached to an outer end of the threaded portion;
such that the slider assembly enables the arm connector portion to slide along the elongated opening when the user lifts or extends the arm.

15. The shoulder brace device of claim 14, wherein the at least one bolt assembly further comprises:
a slider spacer, which comprises a central aperture, such that the slider spacer is mounted between the arm connector portion and the ball joint arm, with the threaded portion of the bolt protruding through the central aperture;
such that the slider spacer enables a smooth sliding motion of the arm connector portion along the elongated opening.

16. The shoulder brace device of claim 11, wherein the ball joint arm comprises:
an offset piece, which is perpendicularly attached to the end of the ball joint arm, such that the offset piece attaches the ball to the ball joint arm, such that the offset piece perpendicularly offsets the ball in respect to the ball joint arm.

17. A shoulder brace device, comprising:
a) a torso band, which is configured to be positioned around a torso of a user;
b) an arm band, which is configured to be positioned around an arm of the user; and
c) a brace mechanism, comprising:
  a main plate, which is configured to connect to the torso band;

an arm plate, which is configured to connect to the arm band; and a ball joint assembly, which comprises:

a ball joint arm, which is connected to the arm plate, such that the ball joint arm comprises a ball that is offset perpendicularly from an end of the ball joint arm; and a ball joint mounter, which is attached to the main plate, such that the ball joint mounter is configured to receive the ball of the ball joint arm, such that the ball joint arm is secured and freely rotatable within the ball joint mounter;

wherein the ball joint assembly enables the arm plate to freely rotate with respect to the main plate, wherein the ball joint mounter comprises:

a left mounting piece, which comprises a spherically curved right inner surface; and a right mounting piece, which comprises a spherically curved left inner surface;

such that the left mounting piece and the right mounting piece are positioned on a left and a right side of the ball, respectively, such that the left mounting piece and the right mounting piece form a ball shaped chamber around the ball;

wherein an upper end of the main plate and an upper end of the arm plate are pivotably connected, such that the brace mechanism is configured to be positionable between the arm and the torso of the user;

such that a lower end of the main plate projects vertically downward, when the shoulder brace device is mounted on the user;

such that the brace mechanism allows movement of the arm, such that the user is enabled to move the arm to adjust the brace mechanism to a comfortable position;

such that the brace mechanism is configured to be lockable in the comfortable position to prevent injuring motions to a healing shoulder.

18. The shoulder brace device of claim 17, wherein the arm plate is slidably attached to the ball joint arm, such that when the arm of the user is lifted laterally, the arm plate slides with respect to the ball joint assembly to provide a necessary extension for the arm of the user to extend.

19. The shoulder brace device of claim 18, wherein the brace mechanism further comprises at least one slider assembly, which comprises:

a) a bolt, which comprises a threaded portion; and
b) a nut, which is attachable to the bolt;

wherein the ball joint arm further comprises an elongated opening wherein the arm plate further comprises a plate aperture;

such that the threaded portion of the bolt is inserted through the elongated opening of the ball joint arm and the plate aperture, such that the at least one slider assembly is secured with the bolt attached to an outer end of the threaded portion;

such that the at least one slider assembly enables the arm plate to slide along the elongated opening when the user lifts or extends the arm.

20. The shoulder brace device of claim 17, wherein the torso band comprises:

at least one torso pocket, such that the at least one torso pocket is configured to receive the main plate; and wherein the arm band comprises:

at least one arm pocket, such that the at least one arm pocket is configured to receive the arm plate;

such that the brace mechanism is configured to be insertable into the arm band and the torso band.

21. The shoulder brace device of claim 17, wherein the torso band comprises:

a) a right torso pocket, which is positioned to align with a right arm of the user when the user is wearing the torso band, such that the right torso pocket is configured to receive the main plate; and b) a left torso pocket, which is positioned to align with a left arm of the user when the user is wearing the torso band, such that the left torso pocket is configured to receive the main plate;

such that the brace mechanism is usable on the left arm and the right arm of the user.

22. The shoulder brace device of claim 17, wherein the brace mechanism further comprises an adjustment assembly, which comprises:

a) a screw, which is insertable through lower ends of the left mounting piece and the right mounting piece, such that the screw extends past a right end of the right mounting piece; and b) an adjustment knob, which is connected to an outer end of the screw, such that the adjustment knob enables adjustment of the screw via a rotation of the adjustment knob;

such that when the screw is turned clockwise by the adjustment knob, the screw moves the left mounting piece closer to the right mounting piece, such that a friction force around the ball in the ball shaped chamber increases;

such that when the screw is turned counterclockwise by the adjustment knob, the screw moves the left mounting piece further from the right mounting piece, such that the friction force around the ball in the ball shaped chamber decreases;

such that the ball joint assembly is tightened to lock the ball joint arm in the comfortable position.

* * * * *